United States Patent [19]

Dobler et al.

[11] Patent Number: 5,015,296

[45] Date of Patent: May 14, 1991

[54] CONTINUOUS EPIMERIZATION OF SUGARS, IN PARTICULAR D-ARABINOSE TO D-RIBOSE

[75] Inventors: Walter Dobler, Heidelberg; Joachim Paust, Neuhofen, both of Fed. Rep. of Germany

[73] Assignee: BASF Aktiengesellschaft, Ludwigshafen, Fed. Rep. of Germany

[21] Appl. No.: 184,805

[22] Filed: Apr. 22, 1988

[30] Foreign Application Priority Data

Apr. 30, 1987 [DE] Fed. Rep. of Germany ....... 3714473

[51] Int. Cl.$^5$ .............................................. C13K 13/00
[52] U.S. Cl. ...................................... 127/42; 427/46.1
[58] Field of Search ....................... 127/46, 42, 58, 61; 536/1.1, 124, 125

[56] References Cited

U.S. PATENT DOCUMENTS

| | | | |
|---|---|---|---|
| 4,029,878 | 6/1977 | Kruse ........................................ | 536/1 |
| 4,263,454 | 4/1981 | Schmidt et al. ...................... | 562/587 |
| 4,292,766 | 10/1981 | Kirk et al. ........................ | 51/105 SP |
| 4,355,158 | 10/1982 | Wolf et al. ............................... | 536/1 |
| 4,602,086 | 7/1986 | Hiroshi et al. ...................... | 536/125 |
| 4,778,531 | 10/1988 | Dobler et al. ....................... | 127/46.2 |

FOREIGN PATENT DOCUMENTS 2311846 12/1976 France .
76894 6/1980 Japan .

OTHER PUBLICATIONS

Chemical Abstract, vol. 110, No. 5, "Continuous Process for the Epimerization of Sugars in Particular of D-Arabinose into D-Ribose", Chem. Ab. No. 39316x, Dobler et al., p. 580, Jan. 30, 1989.

Bilik, Author's Certificate 149, 463, Czechoslovak Socialist Republic, Disclosed on Sept. 29, 1972, Issued on Jul. 15, 1973, "Method of Preparation of L-Glucose by Catalized Epimerization of L-Mannose, or L-Mannose Phenylhydrazone" Translated by Quest Technology, Inc. 1603 S. Highland Ave. Arlington Heights, IL 60005.

Chem. Pharm Bull., vol. 28, (1980), p. 1324, "Epimerization of Aldoses Catalyzed by Dioxobis", Abe et al.

Chem. Abstract, vol. 81: 78189k (1974), "L-Ribose by Catalyzed Epimerization of L-Arabinose", Bilik, p. 487.

Chem. Abstract, Band 97, Nr. 13, 27 (Sep. 1982), Seite 647, 1100335y and JP-A-82 54 198.

Primary Examiner—Theodore Morris
Assistant Examiner—David M. Brunsman
Attorney, Agent, or Firm—Oblon, Spivak, McClelland, Maier & Neustadt

[57] ABSTRACT

Pentoses and hexoses are continuously epimerized by heating a sugar in solution in a solvent in the presence of a basic anion exchanger charged with a molybedenum(VI) compound by preparing a D- or L-sugar having cis-disposed OH groups in the 2- and 3-positions of the sugar by continuously passing a homogeneous solution of the corresponding sugar having transdisposed OH groups in the 2- and 3-positions of the sugar in a mixture of water and methanol or ethanol at from 70° to 100° C., preferably at from 73° and 80° C., through a reaction tube which contains the basic anion exchanger charged with the molybdenum(VI) compound, this method being suitable in particular for epimerizing D-arabinose to prepare D-ribose required for the production of riboflavin.

7 Claims, No Drawings

CONTINUOUS EPIMERIZATION OF SUGARS, IN PARTICULAR D-ARABINOSE TO D-RIBOSE

The present invention relates to a continuous process for epimerizing D- and L-sugars having transdisposed OH groups in the 2- and 3-positions of the sugar, in particular D-arabinose to D-ribose. The D-ribose is required for the synthesis of vitamin $B_2$.

It is known that D-ribose can be prepared by extraction from natural substances, by fermentation of a microorganism or by chemical synthesis (from furan or glucose). All these processes, however, are complicated and give a low yield.

The process used for a long time in industry for preparing D-ribose comprised oxidizing D-glucose with oxygen in an aqueous alkali solution to form D-arabinose, separating off the D-arabinose in the form of a metal salt, for example a mercury or zinc salt, lactonizing to give D-ribonolactone, and reducing with sodium amalgam to D-ribose. The heating of D-arabinose in an aqueous alkali solution gives a mixture containing D-arabonic acid and D-ribonic acid in an equilibrium ratio of 70:30. It is impossible to obtain a D-ribonic acid level higher than 30%. Other problems with the process are due to the use of large amounts of mercury for the amalgam reduction.

Bilik et al. have reported on the epimerizability of various saccharides in aqueous solution in the presence of a molybdenic acid catalyst, including the epimerizability of L-arabinose to L-ribose (cf. Czech Patent No. 149,472; Chemical Abstracts 81, 78189 K).

This knowledge led to the development of a process where D-gluconic acid was oxidized not to D-arabonic acid but to D-arabinose. The oxidizing agent used was hypochlorite. D-arabinose is then epimerized in aqueous solution in the presence of a molybdenum catalyst to D-ribose. (cf. EP 20,959). This process gives an epimerization ratio (proportion of ribose in an equilibrium mixture) of only about 25%. Nevertheless, this process is superior to those described above, since it uses no mercury and fewer steps are required. In one version of the process, a large proportion of the arabinose is separated off in crystalline form and returned into the epimerization.

To facilitate the removal of the molybdenic acid from the epimerization solution, there is prior art describing the use of a molybdenic acid-bearing ion exchanger resin in place of molybdenic acid (cf. U.S. Pat. No. 4,029,878 or DE 2,622,316) or the use of a molybdenic acid-bearing ion exchanger fiber (cf. Japanese Laid-Open Patent Application No. 76 894/1980). The epimerization ratio of D-arabinose/D-ribose is 69.4/30.6. Japanese Laid-Open Patent Application No. 54,197/1982 and 54,198/1982 disclose an epimerization ratio of 27.2% of D-ribose. The processes described employ aqueous sugar solutions.

It is further known that on heating L-arabinose in dimethylformamide in the presence of dioxobis(2,4-pentadionato-O,O'molybdenum(VI) L-arabinose is epimerized to L-ribose to 36% (cf. Abe et al., Chemical and Pharmaceutical Bulletin 28 (1980), 1324).

A further improvement in ribose selectivity was obtained on adding boron compounds in 2-3 times the molar amount to the epimerization mixture (cf. German Laid-Open Application DOS 3,437,571). This gave an epimerization equilibrium of about 60% in aqueous solution and of up to 94% in nonaqueous solution. The use of numerous nonaqueous solvents here was made possible by the formation of boric acid/sugar complexes which were soluble in these solvents. However, this process variant is not very suitable for use in industry, since the boric acid level cannot be reduced to a level tolerable for vitamin $B_2$ production without also removing ribose and arabinose; that is, the yield of total sugars drops substantially with every measure for separating off the boric acid. In addition, removal of the unconverted arabinose from the boric acid solution for reuse is not complete and is accompanied by losses of ribose. Nor is the removal of boric acid by chromatography much more advantageous, since 1) the separating capacity with respect to ribose is substantially reduced by the high boric acid level and 2) the boric acid is responsible for strong broadening of the ribose peak, giving the ribose eluate in very diluted form.

In each of the processes described above the conversion of arabinose was optimized. With the ion exchanger bound catalyst there is additionally no need to separate off a catalyst. However, all these processes give rise to byproducts. These comprise for example in the epimerization of arabinose minor amounts of the 3-epimers lyxose and xylose and a major amount of nonreducing sugar derivatives.

The product distribution described in Japanese Laid-Open Patent Applications 54,197/1982 and 54,198/1982 is 25.1% of ribose, 66.4% of arabinose, 0.6% of lyxose and xylose and 7.9% of nonreducing byproducts.

However, for an ideal process for preparing D-ribose it is not sufficient if only the ribose content in the pentose mixture is as high as possible. Since unconverted arabinose is generally separated off and recycled into the epimerization, it is at least as important to minimize the formation of nonreducing byproducts and of lyxose and xylose. The higher the quantity of unwanted byproduct, the greater the difficulty of an arabinose recycle and the lower the ribose selectivity. If, after the bulk of unconverted arabinose has been separated off by crystallization, the byproducts are bled out of the mother liquor together with the product ribose, this reduces the yield of N-D-ribityl-3,4-xylidine in the next stage of the vitamin $B_2$ synthesis (cf. Merck Patent EP 20,959).

It is an object of the present invention to improve the process for preparing a D-ribose-containing solution from a D-arabinose-containing solution by epimerization in the presence of a molybdenum(VI) compound in such a way that the epimerization equilibrium is shifted in the favor of ribose even without the presence of significant amounts of boric acid. It is a further object of the present invention to develop an epimerization process which is free of the prior art disadvantages and which is also suitable for the epimerization of other pentosenes and hexosenes.

We have found that these objects are achieved, surprisingly, and that the epimerization equilibrium for the epimerization of arabinose to ribose can be shifted in the favor of D-ribose even in the absence of significant amounts of difficult-to-remove boric acid and even without the use of very specific molybdenum compounds, such as dioxibis(2,4-pentanedionato-O,O')-molybdenum(VI) in dimethylformamide, and byproduct formation can be substantially avoided, if the epimerization is carried out at from 70° to 100° C., preferably at from 75° to 80° C., in a mixture of water and methanol or ethanol in the presence of a basic ion exchanger charged with a molybdenum(VI) compound.

The process can to advantage be carried out continuously in industry and can also be used to epimerize other D- and L-sugars having trans-disposed OH groups in the 2- and 3-positions.

The present invention accordingly provides a continuous process for epimerizing a pentose or hexose by heating a sugar in solution in a solvent in the presence of a molybdenum(VI) compound, which comprises preparing a D- or L-sugar of the formula Ia or Ib having cis-disposed OH groups in the 2- and 3-positions of the sugar

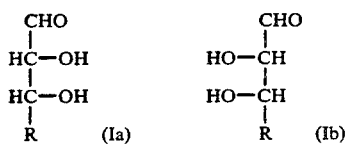

where R is one of the radicals

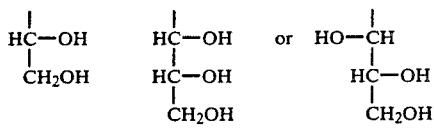

by continuously passing a homogeneous solution of the corresponding sugar of the formula IIa or IIb having transdisposed OH groups in the 2- and 3-positions of the sugar

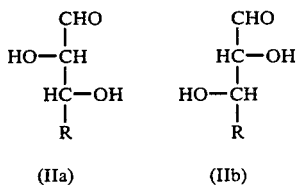

in a mixture of water and methanol or ethanol and in the absence of significant amounts of any boric acid compound at from 70° to 100° C., preferably at from 73° to 80° C., through a reaction tube which contains the basic anion exchanger charged with the molybdenum(VI) compound.

By means of this process it is possible for example to epimerize an approximately 35% strength by weight solution of arabinose in 1:1 methanol/water to D-ribose with a conversion of 35% and a ribose selectivity of 91% without forming detectable amounts of D-lyxose or xylose. The sugar loss is only about 3%. The product solution thus obtained has only a slight yellow color. It can be concentrated to a dry substance content of about 70% to crystallize the bulk of the unconverted arabinose in at least 99% purity, which can be recycled into the epimerization.

The catalyst used for the epimerization is a basic ion exchanger charged with a molybdenum(VI) compound. The use Df such catalysts is known per se (cf. Japanese Laid-Open Application 54,197/1982). Suitable ion exchangers comprise not only weakly basic ones, such as Lewatit MP62, but also those of a strongly basic type, such as Lewatit MP 500. Excellent results are obtained in either case.

The ion exchanger can be charged for example as described in Carbohyd. Res. 153 (1986), 263-270, in particular 270, namely by applying a 0.1M aqueous solution of $(NH_4)_6Mo_7O_{24}$ to the column until there are no longer any detectable $Cl^-$ ions in the eluate.

The resin is then first washed with water and then with the solvent used for the epimerization. However, it is also possible to start from the less costly Mo compounds $MoO_3$ and $H_2MoO_4$, which can be dissolved in aqueous solution with ammonia or $Na_2MoO_4$. The solution is brought to pH 3-7, preferably pH 5-6, to give a corresponding paramolybdate solution. The ion exchanger resin is charged in this way with about 1 mole of Mo per liter of resin.

In the epimerization, the catalyst thus prepared releases only small traces of molybdate, which partly will ultimately return back to the exchanger in the arabinose crystals and partly will be separated from the ribose in the chromatographic purification of the mother liquor from the arabinose crystallization.

The epimerization is carried out in mixtures of water and methanol or ethanol. In principle it is of course also possible to use water, but then the conversion is not high enough for an industrial process. The conversion increases with the alcohol content and in the order: water<methanol<ethanol. However, in selecting the solvent it must also be taken into account that the solubility of arabinose decreases in the order water>methanol>ethanol. In an industrial plant, the product concentration should be as high as possible. On the other hand, it must be ensured that no arabinose will crystallize out in the pipework. Possible ratios for the methanol/water mixture range from 95:5 to about 30:70, preferably from 80:20 to 40:60, in particular about 50:50. If a 50:50 methanol/water mixture is used, it is possible to use for example a 35% strength sugar solution which, even in the event of insufficient insulation and a low linear speed of the solution, is sufficiently far away from the crystallization point. If ethanol is used, somewhat more water is required in the mixture. Possible ethanol:water ratios range from 85:15 to 30:70, preferably from 70:30 to 50:50.

The residence time of the sugar solution over the catalyst is in general within the range from about 30 to 120 minutes, preferably from 60 to 80 minutes. It is dependent on the reaction temperature. In general terms it can be stated that shorter residence times go together with temperatures above 80° C., while temperatures below 80° C. require longer residence times. It is a great advantage of the process according to the invention that even at the preferred low temperatures of from 73° to 80° C., where byproduct formation is extremely low and the widely used ion exchangers are capable of continuous operation without being damaged, no excessively long residence times are required. Overly long residence times lead to increased sugar loss and to the appearance of lyxose and xylose, i.e. they reduce the selectivity and life of the catalyst. The residence time in a continuous process is regulated for a given reactor length by means of the flow rate.

The epimerization process according to the invention is employable to the following epimerization equilibria:

| (1) | Arabinose | (IIa) | → | Ribose   | (Ia) |
|-----|-----------|-------|---|----------|------|
| (2) | Xylose    | (IIb) | → | Lyxose   | (Ib) |
| (3) | Glucose   | (IIb) | → | Mannose  | (Ib) |
| (4) | Galactose | (IIb) | → | Talose   | (Ib) |
| (5) | Altrose   | (IIa) | → | Allose   | (Ia) |

| (6) Idose | (IIa) | → | Gulose | (Ia) | the epimerization of altrose and idose being less important, since these sugars are themselves difficult to obtain.

However, the process according to the invention is of very particular importance when used for preparing a predominantly D-ribose-containing solution by epimerization of a D-arabinose-containing solution, since on the one hand ribose is a much sought after sugar and on the other this epimerization gives the greatest advantages.

The present invention therefore also provides a continuous process for epimerizing a D- or L-sugar by heating D-arabinose in solution in a solvent in the presence of a molybdenum(VI) compound, which comprises preparing D-ribose by continuously passing a homogeneous solution of D-arabinose in a mixture of water and methanol or ethanol at from 70° to 100° C., preferably at from 73° to 80° C., in the absence of any significant amounts of a boric acid compound through a reaction tube which contains a basic anion exchanger charged with the molybdenum(VI) compound.

In a preferred embodiment, the process according to the invention is carried out as follows: an approximately 30–40% strength by weight aqueous/alcoholic sugar solution is passed at from 80° to 85° C. through the reaction tube filled with the basic ion exchanger in molybdate form. The solution emerging from the reaction tube is continuously concentrated by evaporation from a dry substance content of about 40% to a dry substance content of about 65–70%. By addition of small amounts of methanol and cooling down to 0° C. the bulk of unconverted arabinose is made to crystallize out and, after having been separated off and washed, is recycled into the epimerization.

The mother liquor obtained after concentrating, which contains about 65–70% of ribose, is split in a conventional manner (cf. J. Angyal et al., Carbohyd. Res. 73 (1979), 9–18 and references cited therein) over a strongly acid ion exchanger in the Ca$^{2+}$ form into 3 fractions which contain the following compounds:

1) byproducts, including trace molybdate (waste disposal)
2) arabinose and ribose, which are recycled into the arabinose crystallization stage and
3) ribose having a purity of more than 99.9% (?).

The process according to the invention has many advantages over the existing process.

1) No lyxose or xylose is formed, as a result of which less sugar is lost, nor are these sugars concentrated to interfering levels in the circulation system of the continuous process.
2) As little byproduct is formed, less arabinose is lost and less waste product needs to be disposed of.
3) The low proportion of byproducts is removed by chromatographic purification, preventing any buildup in the product cycle.
4) All the arabinose can be recycled, which increases the ribose selectivity.
5) The arabinose and the ribose spontaneously crystallize out even from water as a consequence of their high purity after concentrating.
6) By using methanol/ or ethanol/water mixtures the reaction can even be carried out advantageously at from 73° to 80° C., where the widely used anion exchangers are capable of continuous operation without damage.

EXAMPLES 1 AND 2

The epimerization was carried out in a temperature-controllable tube (ID 25 mm, L=1000 m=bed height of ion exchanger), through which a hot solution of arabinose in 1) (1/1) CH$_3$OH/H$_2$O or 2) (85/15) C$_2$H$_5$OH/H$_2$O was pumped at rates of 5–10 ml/min.

The concentration of reducible sugar was determined by the method of Luff-Schorl. The ratio of ribose/lyxose/xylose/arabinose was determined by HPLC (two 30×0.2 mm carbohydrates connected in series, CH$_3$CN/H$_2$O=98/12, 50° C., 1.5 ml/min, RI).

The preparative chromatography of the mother liquor which contained approximately 70% of ribose after the bulk of unconverted arabinose had been separated off and after concentrating was carried out at 60° C. and at 33 ml of H$_2$O/min over a strongly acid ion exchanger in the Ca$^{2+}$ form using a 6.3×800 mm column. The ribose was obtained in a purity of more than 99.9%.

Results of continuous epimerization over molybdate-charged Lewatit MP62:

|  | (a) CH$_3$OH/H$_2$O (1/1) 80° C.: 35% strength by weight solution [%] | (b) C$_2$H$_5$OH/H$_2$O (85:15) 75° C.: 10% strength by weight solution [%] |
|---|---|---|
| D-ribose | 31.9 | 37.2 |
| D-arabinose | 65.0 | 60.0 |
| D-lyxose/xylose | ≦0.1* | ≦0.1* |
| Sugar loss | 3.1 | 2.8 |
| Conversion | 35 | 40 |
| Selectivity | 91 | 93 |

*= Not detectable by HPLC even though column was overloaded.

We claim:

1. A continuous process for epimerizing a pentose or hexose by heating a sugar in solution in a solvent in the presence of a basic anion exchanger charged with a molybdenum (VI) compound, which consists essentially of preparing a D- or L-sugar of the formula (Ia) or (Ib) having cis-disposed OH groups in the 2- and 3-positions of the sugar:

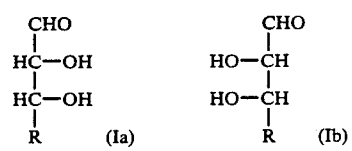

wherein R is one of the radicals of the formula:

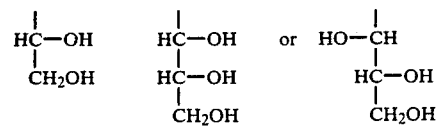

by continuously passing a homogeneous solution of the corresponding sugar of the formula (IIa) or (IIb) having trans-disposed OH groups in the 2- and 3-positions of the sugar:

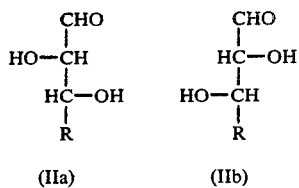

(IIa)  (IIb)

in a mixture of water and methanol or water and ethanol through a reaction tube which contains the basic anion exchanger charged with the molybdenum (VI) compound, and further wherein said methanol and water are used in a ratio of about 95:5 to 30:70, respectively, and said ethanol and water are used in a ratio of about 85:15 to 30:70, wherein the conversion is equal or greater than about 35%.

2. The process as claimed in claim 1, wherein a solution of the sugar of the formula IIa or IIb is heated in a mixture of from 5 to 70% by weight of water and from 5 to 30% by weight of methanol.

3. The process as claimed in claim 1, wherein the solution of the sugar in the mixture of water and methanol or ethanol is continuously passed at from 75° to 80° C. through the reaction tube which contains the basic anion exchanger charged with the molybdenum (VI) compound.

4. The process as claimed in claim 1, wherein, to prepare D-ribose of the formula (Ia), the solution of D-arabinose of the formula (IIa) in a mixture of water and methanol or ethanol is passed at from 70° to 100° C. through the reaction tube which contains the basic anion exchanger charged with the molybdenum (VI) compound.

5. The process as claimed in claim 1, wherein, to prepare D-ribose of the formula (Ia), the solution of D-arabinose of the formula (IIa) in a mixture of water and methanol or ethanol is passed at from 73° to 80° C. through the reaction tube which contains the basic anion exchanger charged with the molybdenum (VI) compound.

6. The process as claimed in claim 4, wherein, D-ribose of the formula (Ia) is prepared by:
  a) passing the solution of D-arabinose of the formula (IIa) in a mixture of water and methanol or ethanol at from 73° to 80° C. through a reaction tube which contains the basic ion exchanger charged with the molybdenum (VI) compound, then
  b) concentrating the eluate thereby obtained to a dry substance content of about 65 to 70% by weight,
  c) adding methanol or ethanol thereto, and cooling the mixture thereby obtained to about 0° C. in order to cause the unconverted arabinose to crystallize, and separating off the crystallized unconverted arabinose and recycling the same,
  d) concentrating and purifying the filtrate obtained by separating the unconverted arabinose using a strongly acidic ion exchanger in the $Ca^{+2}$ form, and
  e) recycling the by-product-free fraction containing a mixture of arabinose and D-ribose obtained during said purification step into the arabinose crystallization stage.

7. The process as claimed in claim 1, wherein said methanol and water are used in a ratio of about 80:20 to 40:60, and said ethanol and water are used in a ratio of about 70:30 to 50:50.

* * * * *